United States Patent
Vilsmeier (10) Patent No.: US 9,925,392 B2
(45) Date of Patent: *Mar. 27, 2018

(54) BREATHING PHASE-BASED TRANSFORMATION OF A STATIC COMPUTED TOMOGRAPHY

(71) Applicant: Brainlab AG, Munich (DE)

(72) Inventor: Stefan Vilsmeier, Munich (DE)

(73) Assignee: Brainlab AG, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/505,819

(22) PCT Filed: Aug. 27, 2015

(86) PCT No.: PCT/EP2015/069672
§ 371 (c)(1),
(2) Date: Feb. 22, 2017

(87) PCT Pub. No.: WO2016/030470
PCT Pub. Date: Mar. 3, 2016

(65) Prior Publication Data
US 2017/0246478 A1 Aug. 31, 2017

Related U.S. Application Data

(63) Continuation of application No. PCT/EP2014/068244, filed on Aug. 28, 2014.

(51) Int. Cl.
*G06K 9/36* (2006.01)
*G06K 9/32* (2006.01)
(Continued)

(52) U.S. Cl.
CPC ............ *A61N 5/1037* (2013.01); *A61B 6/032* (2013.01); *A61B 6/486* (2013.01); *A61B 6/50* (2013.01);
(Continued)

(58) Field of Classification Search
None
See application file for complete search history.

(56) References Cited

U.S. PATENT DOCUMENTS

2005/0201510 A1* 9/2005 Mostafavi ............ A61B 5/7292
378/8
2006/0074292 A1 4/2006 Thomson
(Continued)

FOREIGN PATENT DOCUMENTS

WO 2014048490 4/2014

OTHER PUBLICATIONS

Schweikard A et al., "Respiration tracking in radiosurgery without fiducials", International Journal of Medical Robotics and Computer Assistedsurgery, John Wiley, vol. 1, No. 2, Jan. 1, 2005.
(Continued)

*Primary Examiner* — Randolph I Chu
(74) *Attorney, Agent, or Firm* — Middleton Reutlinger (57) ABSTRACT

Disclosed is a medical data processing method of determining a transformation for determining a breathing state-dependent geometry of an anatomical body part of a patient's body, the method comprising executing, on at least one processor of at least one computer, steps of: a) acquiring, at a processor, planning image data describing a set of tomographic medical planning images describing each a different part of the anatomical body part in the same respiratory state called reference planning respiratory state (y), wherein the anatomical body part is subject to respiratory movement and wherein the planning images comprise a planning image called reference planning image describing a part of the anatomical body part which is called reference planning body part; b) acquiring, at a processor, breathing image data describing a set (1) of tomographic medical breathing images of the anatomical body part, wherein the breathing images comprise a reference breathing image (A) describing the reference planning body part in a respiratory state called reference breathing respiratory state (a), which is different from the reference planning respiratory state (y), and a target breathing image (C) describing at least another part of the anatomical body part, wherein the other part of the anatomical body part is called target body part, in a respiratory state called target respiratory state (c) which is different from the reference planning respiratory state; c) determining, by a processor and based on the planning image data and the breathing image data, reference trans-
(Continued)

formation data describing a transformation, called reference transformation (R), between the geometry (Factor A) of the reference planning body part in the reference planning respiratory state (y) and the geometry of the reference planning body part in the reference breathing respiratory state (a); d) acquiring, at a processor, scaling factor data describing a scaling factor (sf) which describes a relationship between the geometry (Factor A) of the reference planning body part in the reference breathing respiratory state (a) and the geometry (Factor C) of the target body part in the target respiratory state (c); e) determining, by a processor and based on the reference transformation and the scaling factor data, derived transformation data describing a transformation called derived transformation (T) between the geometry of the target body part in the reference planning respiratory state (y), and the geometry (Factor C') of the target body part in the reference breathing respiratory state (a).

16 Claims, 2 Drawing Sheets

(51) Int. Cl.
*G01B 11/26* (2006.01)
*G01C 1/00* (2006.01)
*A61N 5/10* (2006.01)
*A61B 6/03* (2006.01)
*A61B 6/00* (2006.01)

(52) U.S. Cl.
CPC ......... *A61N 5/1065* (2013.01); *A61N 5/1068* (2013.01); *A61N 5/1077* (2013.01)

(56) References Cited

U.S. PATENT DOCUMENTS

| 2008/0221439 | A1* | 9/2008 | Iddan | A61B 6/5217 600/424 |
| 2014/0275962 | A1* | 9/2014 | Foo | A61N 2/002 600/411 |

OTHER PUBLICATIONS

European Patent Office, International Search Report and Written Opinion for PCT/EP2014/068244 dated May 19, 2015.
European Patent Office, International Search Report and Written Opinion for PCT/EP2015/069672 dated Oct. 28, 2015.

\* cited by examiner

BREATHING PHASE-BASED TRANSFORMATION OF A STATIC COMPUTED TOMOGRAPHY

The present invention is directed to a medical data processing method of determining a transformation for determining a breathing state-dependent geometry of an anatomical body part of a patient's body, a corresponding computer program, a computer running that program and a radiotherapy system or radiosurgery system comprising that computer or a system comprising an imaging apparatus and that computer.

When conducting radiotherapy or radiosurgery, respectively, it is desirable to know where the treatment body part which shall be irradiated with ionising radiation is located when the beam is activated. A treatment body part which is positioned in the thorax or abdomen, respectively, is subject to respiratory movement so that its position is generally not known while the patient is breathing.

Previous approaches to determining the position of the treatment body part include taking a computed tomography of the treatment body part while the patient is breathing freely and has marker devices fixedly attached to the thorax. The marker devices are tracked with an optical tracking system to determine their position during respiratory movement of the thorax. These positions are time-correlated with the time passed during acquisition of the computed tomography and thereby allow for determining the position of the treatment body part at a specific point in time during the patient's respiratory cycle if the marker devices are again attached to the patient's thorax and tracked during therapy. However, that approach requires use of a number of devices such as a tracking system during therapy. Furthermore, the patient is subjected to a comparably high radiation dose during acquisition of the computed tomography.

The present invention therefore provides a medical data processing method for determining a positional transformation of the position of a treatment body part shown in an image into the position it would have at a specific respiratory state. This method allows for example to at least partly avoid the radiation dose applied to a patient for generation of a four-dimensional planning tomography of the treatment body part.

Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature. A feature of one embodiment which adds an additional function to another embodiment can for example be added to said other embodiment.

The present invention has for example application in a radiotherapy system, such as with Brainlab's radiosurgery products, for example Brainlab's software modules called "Elements" which constitute a software application which is suitable for example for use on a desktop computer or as cloud service on a mobile device. Elements provide a radiotherapy and/or radiosurgery planning functionality. An advantage of using the present invention in such an application is that any department with a conventional tomography device is enabled to generate a four-dimensional tomography (e.g. a computed x-ray tomography) which describes the movement in space and time of an anatomical body part which is subject to a vital movement such as respiratory movement. Application of the disclosed method drastically reduces the radiation dose which would be applied to the patient for generation of such a four-dimensional tomography using conventional methods.

EXEMPLARY SHORT DESCRIPTION OF THE PRESENT INVENTION

In the following, a short description of the specific features of the present invention is given which shall not be understood to limit the invention only to the features or a combination of the features described in this section.

The disclosed method is directed in particular to determining a spatial transformation of an image contained in a planning computed tomography (called planning CT) which was taken in one (static) respiratory state, e.g. while the patient was holding his breath, into another breathing state which the patient may attain during free breathing and which is associated with an image contained in a free-breathing computed tomography (called breathing CT) which was taken while the patient was breathing freely. To this end, a first spatial transformation (called reference transformation) is determined between one image of the planning CT and one image of the breathing CT. The image of the breathing CT is not associated with the static respiratory state but depicts the same anatomical structure as the image from the planning CT. A scaling factor is used to scale the geometry of the anatomical structure shown in the image of the breathing CT into the geometry of another anatomical structure show in another image of the breathing CT which is associated with another respiratory state (which is also different from the static respiratory state). The reference transformation R is combined with the scaling factor in order to determine a derived transformation T which can be applied to an image of the planning CT showing the other anatomical structure in order to determine the difference between the positions of the other anatomical structure in the images of the planning CT and the breathing CT.

GENERAL DESCRIPTION OF THE PRESENT INVENTION

In this section, a description of the general, in some cases particular preferred, features of the present invention is given.

In a first aspect, the invention is direct to a medical data processing method of determining a transformation for determining a breathing state-dependent geometry of an anatomical body part of a patient's body, the method comprises for example the following steps which are constituted to be executed by a computer, specifically at least one computer. The steps of acquiring and determining data are executed by at least one processor of the at least one computer, For example, the method may be executed by a plurality of processors of one computer or a plurality of computers each having one or more processors.

For example, planning image data is acquired which describes (in particular defines) a set of planning images. The planning images are tomographic medical images, i.e. medical images which have been generated by application of a tomographic medical imaging modality such as computed x-ray tomography (CT) or magnetic resonance tomography (MRT) to a patient's body. Therefore, the planning images contain image information which is associated with information about a three-dimensional position of the structures depicted in the planning images. In one example, the planning images describe (specifically, represent an image of) each a different part of the anatomical body part (i.e. sections of the same anatomical body part which in general are disjunct and/or non-overlapping). The anatomical body part is subject to respiratory movement, i.e. a substantially cyclic movement due to the breathing function of the human body. The anatomical body part is for example at least part of the lung or at least part of the diaphragm. The different parts of the anatomical body are described by the planning images in at least substantially (i.e. within an acceptable degree of deviation from) the same respiratory state (i.e. all the different parts are shown in the same respiratory phase of breathing cycle of the patient). In other words, all planning images are associated with at least substantially the same respiratory state. This respiratory state is also called reference planning respiratory state. For example, medical image data is generated while the patient remains in the same respiratory phase (i.e. while his breathing remains static), for example by holding his breath in a state of at least substantially complete exhalation or at least substantially complete inhalation. Alternatively, the planning image data may have been generated from medical image data associated with another respiratory state if it has been assured by other means that all the images selected for the planning image data are associated with the same respiratory state. For example, the medical imaging apparatus (such as an x-ray tomography apparatus or an MR tomography apparatus) moves relative to the anatomical body part during generation of the medical image data which serves as a basis for generation of the planning image data. Thus, slice images of neighbouring and at least substantially non-overlapping sections of the anatomical body part are generated. The planning images comprise a planning image called reference planning image describing (for example showing) one of the different parts of the anatomical body part which is called reference planning body part.

As a further exemplary step, breathing image data is acquired which describes (in particular defines) a set of tomographic medical breathing images of the anatomical body part. The breathing images have been generated by application of a tomographic medical imaging modality as described above with regard to the planning image data. The set of breathing images in one example comprises image information for (all) the parts of the anatomical body part described by the planning images. The difference compared to the planning images is however, that the breathing image data is generated based on imaging the patient not while his breathing remains static. Rather, the patient desirably breathes at least substantially normally, for example as rehearsed beforehand, while he is being imaged for acquisition of the data serving as a basis for generation of the breathing image data. The respiratory states with which the breathing images are associated therefore are all at least substantially different from the reference planning respiratory state. In one example, the breathing images comprise an image called reference breathing image describing (for example showing) the reference planning body part in a respiratory state called reference breathing respiratory state. The reference breathing respiratory state also is at least substantially different from the reference planning respiratory state. Furthermore, the breathing images comprise an image called target breathing image describing at least another part of the anatomical body part (i.e. a part of the anatomical body part which is at least substantially different from the reference body part) which is called target body part. The target breathing image describes (for example shows) the target body part in a respiratory state which is called target respiratory state and which is at least substantially different from the reference planning respiratory state. The target respiratory state in general is different from the reference breathing respiratory state, but the disclosed method can also deal with the case of the target respiratory state being identical to the reference breathing respiratory state.

In a further exemplary step, reference transformation data is determined based on the planning image data and the breathing image data, for example based on the reference planning image and the reference breathing image. The reference transformation data describes (in particular defines) a transformation (called reference transformation) between the geometry of the reference planning body part in the reference planning respiratory state and the geometry of the reference planning body part in the reference breathing respiratory state, i.e. between the geometry of the reference planning body part as it is described by the reference planning image and the geometry of the reference planning body part as it is described by the reference breathing image. In other words, the reference transformation may be considered to be a transformation between the reference planning image and the reference breathing image. The term of geometry within the meaning of this disclosure encompasses at least one of the position, the size and shape of the body parts which are defined in the medical images for example by specific image features and/or the spatial relationship of specific image features relative to one another.

Within this disclosure, a transformation is understood to be a spatial (for example positional) transformation such as a mapping, for example a coordinate mapping which may be embodied by a mapping matrix. The reference transformation is a transformation between the reference planning image and the reference breathing image. For example, the reference transformation defines a spatial relationship between the image features of the reference planning image and the reference breathing image. In one example, the reference transformation is determined by applying a fusion algorithm to the reference planning image and the reference breathing image which comprises registering, for example elastically fusing, these images to each other.

In a further exemplary step, scaling factor data is acquired which describes (in particular defines) a scaling factor which describes a relationship between the geometry of the reference planning body part in the reference breathing respiratory state (i.e. of the geometry of the reference planning body part as it is described by the reference breathing image) and the geometry of the target body part in the target respiratory state (i.e. of the geometry of the target breathing body part as it is described by the target breathing image). The geometry of the reference planning body part and of the target body part are represented in this algorithm for example by a scalar value, or a vector or a matrix containing entries which defines or define, respectively, the respective geometry.

For example, the breathing image data comprises a further image called comparative breathing image describing a further part of the anatomical body part in the reference breathing respiratory state, which further part is called comparative breathing body part and is different from (for example not identical to) the reference body part and the target body part.

In this example, the further optional steps can be executed: For example, imaging movement data describing (in particular defining) the movement of the medical imaging apparatus relative to the anatomical body parts while it is being used for generating the breathing medical images.

The movement of the medical imaging apparatus can be defined by its moving speed relative to the anatomical body part which is known from the operating parameters of the medical imaging apparatus. Furthermore, respiratory cycle data is acquired describing (in particular defining) the time period required by the patient for a respiratory cycle (in particular during normal breathing). This time period can be determined by measuring time with conventional means and measuring the position of surface features on an anatomical structure subject to respiratory movement, e.g. on the belly. The latter can be done by eyesight tracking of the skin on the thorax or by using a medical tracking system to optically track markers (e.g. retroreflective or active—i.e. light-emitting-markers) attached to the thorax e.g. with a marker belt which is wrapped around the belly. The comparative breathing image is the determined (for example selected) from the breathing images based on the imaging movement data and the respiratory cycle data. For example, a breathing image associated with the same breathing phase as the reference breathing image is selected as the comparative breathing image. For example, the comparative breathing image is acquired (selected) from the breathing images based on the imaging movement data and a consistency optimization that uses metrics derived from the reconstructed datasets. The consistency optimization may encompass a check whether the comparative breathing image is different from the reference breathing image.

The step of acquiring the scaling factor data comprises in this example:
acquiring image spacing data describing (in particular defining) the spatial relationship, for example the distance, between the positions (of the medical imaging apparatus) at which the reference breathing image, the target breathing image and the comparative breathing image were generated; and
determining the scaling factor data based on the image spacing data and the reference breathing image data.

The spatial relationship is in one example defined as the ratio r of
the distance between the positions (of the medical imaging apparatus) at which the reference breathing image and the target breathing image were generated, and
the distance between the positions (of the medical imaging apparatus) at which the reference breathing image and the comparative breathing image were generated.

Therefore, the following equations hold:
(1) r=0 if the comparative breathing image is equal (identical regarding its image information) to the reference breathing image;
(2) r=1 if the comparative breathing image is equal (identical regarding its image information) to the target breathing image.

A factor called target factor can then be determined by multiplying (1−r) by the geometry of the reference planning body part in the reference breathing respiratory state, i.e. the geometry of the reference planning body part described by the reference breathing image, and adding thereto the product of r and the geometry of the comparative breathing body part in the reference breathing respiratory state, i.e. the geometry of the comparative breathing body part as it is described by the comparative breathing image.

Alternatively, the target factor is determined based on a function describing the expected geometries of different parts of the anatomical body part as a function of the position of the breathing image showing a part of the anatomical body part in the set of breathing images under the assumption that that part of the anatomical body part is in the reference planning respiratory state. The position of that breathing image is determined for example by the position which a medical imaging apparatus had when it generated the breathing image data. In the simplest case this function may be represented by a straight line going through the values of the function describing the geometry of the reference planning body part in the reference planning respiratory state (as it is shown in the reference breathing image) and the geometry of the comparative body part in the reference planning respiratory state (as it is shown in the comparative breathing image). For example, the position of the reference planning body part is described by its position along the cranial-caudal axis of the lung, and the geometry of the reference breathing body part is described by the average length of the vectors in the reference transformation at the respective position of the reference planning body part; and the position of comparative breathing body part is described by its position along the cranial-caudal axis of the lung, and the geometry of the comparative breathing body part is described by the average length of the vectors in the reference transformation at the respective position of the comparative breathing body part.

Specifically, the function may be determined as FactorC', where $$FactorC' = FactorA \cdot \frac{posC - posB}{posA - posB} + FactorB \cdot \frac{posC - posA}{posB - posA} \quad (1)$$

and where
FactorA is the geometry of the reference planning body part shown in the reference breathing image (i.e. in the reference planning respiratory state);
FactorB is the geometry of the comparative body part shown in the comparative breathing image (i.e. in the reference planning respiratory state);
FactorC' is the geometry of the target body part in the reference breathing respiratory state;
posA is the position of the reference breathing image;
posB is the position of the comparative breathing image;
posC is the position of the target breathing image.

Alternatively, the function may be a higher-order polynomial function (of order >1, i.e. having at least one non-zero square term in it). Such a polynomial function can be derived from a plurality of predetermined (patient-independent) four-dimensional computed tomographies and may therefore consider anatomic and physiological anomalies or influences which cannot be represented by a linear function (i.e. a polynomial of order 0 or order 1).

As a further example, the function may depend on more than one variable, which may be the case if it is represented by a vector or a matrix representing a geometry.

The geometry of the comparative breathing body part is in this algorithm represented for example by a scalar value, or a vector or a matrix containing entries which defines or define, respectively, the respective geometry. For example, a scalar value may be derived for a body part by using the average length of all vectors from the transformation data in the body part. A vector or matrix may vary the factor depending on its position, depending, but not limited to the distance from the spine, heart, position in the lung or other factors. For example vectors or matrices which are subject to undesired influences (such as vectors or matrices which are close to the trachea or close to the heart) are weighted (for example with relatively lower weights or ignored for example by setting their associated weight to zero), and vectors or matrices which represent a relatively larger amplitude of respiratory motion are favoured for example by associating them with relatively larger weights when they are used to determine the target factor. The scaling factor is then determined by dividing the target factor by the geometry of the target body part in the target respiratory state, i.e. by the geometry of the target body part described by the target breathing image. In case the geometry is described by a vector or a matrix, the division is carried out for each entry of the vector or matrix or by using a dedicated function to transform the values.

The scaling factor also considers the geometric and anatomical conditions in the thorax or abdomen, respectively. For example, the scaling factor considers that different breathing images show different anatomical structures, which do not reach the same amplitude during respiratory movement. The derivation of the scaling factor can be limited to certain organs, for example the lung or the diaphragm.

In another example, the scaling factor is predetermined, for example it is the result of an analysis of a plurality of conventional four-dimensional tomographic image sets (i.e. sets of tomographic images which are associated with three-dimensional positional information and time information) taken for a plurality of patients describing respiratory movement. The scaling factor may be stored in a database from which it is read for its acquisition during execution of the disclosed method. The predetermined scaling factor may depend on other data known about the patient, for example including but not limited to age, sex, lung volume or other information.

In a further exemplary step, derived transformation data is determined based on the reference transformation and the scaling factor data. The derived transformation data describes (in particular defines) a transformation called derived transformation. For example, the derived transformation is determined by multiplying the reference transformation component-wise by the scaling factor. The derived transformation is a transformation between the geometry of the target body part in the reference planning respiratory state, i.e. the geometry of the target body part as it is described in one of the planning images (that image is also called target planning image), and the geometry of the target body part in the reference breathing respiratory state, i.e. the geometry of the target body part as it would be described by an image associated with the reference breathing respiratory state. The planning images include the target planning image which is also associated with the reference planning respiratory state. Therefore, positional information defining the positions of its image features can be transformed (by application of the derived transformation to the positional information) into the positions these image features would attain in the reference breathing respiratory state. The position of the target body part (indicated for example by an image of the reference body part) in the reference breathing respiratory state can then as an optional step of the disclosed method be determined by selecting the target planning image and subjecting it to the derived transformation (in other words, by applying the derived transformation to the image features describing the target body part which are contained in the target planning image).

The scaling factor may be valid for the target breathing image only, and the derived transformation may in this sense be determined locally, i.e. individually for each target breathing image (for example, in an iterative procedure over the whole tomographic image data set, specifically over the whole breathing image data).

In another example, the breathing image data was generated over the whole length of at least one breathing cycle of the patient (e.g. for each respiratory state of the patient, there is at least one breathing image). The method can then be executed repeatedly until a breathing image has been used as a reference breathing image for each of the respiratory states described by the breathing image data (in particular for each of the respiratory states associated with the breathing images) in order to receive a derived transformation for all parts of the anatomical body parts described by the planning images into all breathing states. For example, the disclosed method is executed repeatedly until each breathing image has been used at least once as the reference breathing image.

In a further example, the method is used for eliminating an artefact contained in a slice image contained in a set of tomographic medical image data (for example a computed x-ray tomography or a magnetic resonance tomography such as the set of tomographic medical breathing images), wherein the reference planning respiratory state is for example an exhalation state, and wherein one of the tomographic medical breathing images including the artefact is selected as the target breathing image in the target respiratory state, and another one of the tomographic medical breathing images not containing the artefact is selected as the reference breathing image. For implementing this example, both the planning image data and breathing image data can be taken from different phases of a four-dimensional computed tomography (4DCT). Because 4DCTs often span more than one breathing cycle, there is a possibility of different inhalation and exhalation levels present in the images. This can lead to artefacts in the resulting images where the breathing level of one image in one respiratory state does not match the breathing level of the neighbouring slice or slices in the same respiratory state. Often the full exhalation state will have fewer or no artefacts. By selecting a specific respiratory state, for example the exhalation state, as a reference planning respiratory state (planning image data), other respiratory states of the reference planning body part can be described by the breathing image data. In case of an artefact, one of the slice images including the artefact (for example the target breathing image C) is selected so that its state is the reference breathing respiratory state. The other slice is selected to be the reference breathing image A. For both slices A and C, the factors are calculated (FactorA and FactorC). The reference transformation R for determining Factor A may differ from the reference transformation R for determining Factor C. FactorC can then be scaled with the scaling factor sf to determine the derived transformation T from the reference transformation R that transforms the target breathing image C into the reference breathing respiratory state of the reference breathing image A. Subjecting FactorC to the derived transformation T will transform FactorC into FactorC' (this step is not necessarily part of the disclosed method, but may also form part of the disclosed invention). Alternatively, a third slice image can be selected as the comparative breathing image B in the same respiratory state as the reference breathing image A (which is associated with the reference breathing respiratory state). The scaling factor sf can then be determined (specifically, estimated) as described by using the relative position of the target breathing image C between the reference breathing image A and a comparative breathing image B. By repeatedly following this approach, unsuitable respiratory states can be transformed into suitable respiratory states, thus eliminating errors from the 4DCT.

In a second aspect, the invention is also directed to a program which, when running on a computer, causes the computer to perform one or more or all of the method steps described herein and/or to a program storage medium on which the program is stored (for example in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

In a third aspect, the invention is directed to a radiotherapy system or radiosurgery system, comprising:
a treatment beam source (comprising e.g. a linear accelerator, an x-ray tube or a radioactive agent for emission of treatment radiation);
a patient support unit (such as a table, for example a treatment table, or a so-called couch, the position of which is for example automatically controllable); and
the aforementioned computer, the computer being operatively connected to the treatment beam source and the patient support unit to execute the aforementioned program which comprises code means for executing the method according to the first aspect.

In one example, the planning image data serves as a basis for planning a radiotherapeutic or radiosurgical procedure. That means that for example the planning image data is used to determine a geometry (at least one of diameter and direction) of at least one treatment beam used to deliver treatment radiation to a treatment body part (a treatment target) contained for example in the reference body part. For example, the computer is configured to control the treatment beam source to emit a treatment beam based on the derived transformation data. In doing so, the patient is allowed to continue breathing normally during radiotherapy or radiosurgery while it is ensured that the treatment beam source is activated only at instances (points in time) at which the treatment body part is known to be at a predetermined position at which it shall be irradiated with treatment radiation. Thereby, undesired irradiation of anatomical body parts other than the treatment body part can be avoided or at least minimized.

In a fourth aspect, the invention is directed to a system, comprising:
an imaging apparatus (e.g. a computer x-ray tomograph or a magnetic resonance tomograph) for generating the planning image data and the breathing image data; and
the aforementioned computer which is operatively coupled to the imaging apparatus to receive the planning image data and the breathing image data from the imaging apparatus.

The method according to the first aspect can be used in conjunction with for example the system according to the fourth aspect during a diagnostic procedure.

It is within the scope of the present invention to combine one or more features of one or more embodiments or aspects of the invention in order to form a new embodiment wherever this is technically expedient and/or feasible. Specifically, a feature of one embodiment which has the same or a similar function to another feature of another embodiment can be exchanged with said other feature, and a feature of one embodiment which adds an additional function to another embodiment can for example be added to said other embodiment.

The present invention in one example does not involve or for example comprise or encompass an invasive step which would represent a substantial physical interference with the body requiring professional medical expertise to be carried out and entailing a substantial health risk even when carried out with the required professional care and expertise. For example, the invention does not comprise a step of positioning a medical implant in order to fasten it to an anatomical structure or a step of fastening the medical implant to the anatomical structure or a step of preparing the anatomical structure for being fastened to the medical implant. More particularly, the invention does not involve or for example comprise or encompass any surgical or therapeutic activity. The invention is instead directed for example to a method of detecting the position of a body surface without the need for any surgical or therapeutic activity for executing the method. No surgical or therapeutic step is necessitated or implied by carrying out the invention.

Definitions

This section contains definitions for specific terminology used in this disclosure. These definitions also form part of the present disclosure.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is for example a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The present invention relates to for example the field of controlling a treatment beam. The treatment beam treats body parts which are to be treated and which are referred to in the following as "treatment body parts". These body parts are for example parts of a patient's body, i.e. anatomical body parts.

The present invention relates to the field of medicine and for example to the use of beams, for example radiation beams, to treat parts of a patient's body, which are therefore also referred to as treatment beams. For example, the treatment beam comprises or consists of ionising radiation. The ionising radiation comprises or consists of particles (for example, sub-atomic particles or ions) or electromagnetic waves which are energetic enough to detach electrons from atoms or molecules and so ionise them. Examples of such ionising radiation include x-rays, high-energy particles (high-energy particle beams) and/or ionising radiation emitted from a radioactive element. The treatment radiation, for example the treatment beam, is for example used in radiation therapy or radiotherapy, for example in the field of oncology. For treating cancer for example, parts of the body comprising a pathological structure or tissue such as a tumour are treated using ionising radiation. The tumour is then an example of a treatment body part.

The method in accordance with the invention is for example a data processing method. The data processing method is for example performed using technical means, for example a computer. The data processing method is for example constituted to be executed by or on a computer and for example is executed by or on the computer. For example, all the steps or merely some of the steps (i.e. less than the total number of steps) of the method in accordance with the invention can be executed by a computer. The computer for example comprises a processor and a memory in order to process the data, for example electronically and/or optically. The calculating steps described are for example performed by a computer. Determining steps or calculating steps are for example steps of determining data within the framework of the technical data processing method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is for example connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing imaging methods), wherein the technical signals are for example electrical or optical signals. The technical signals for example represent the data received or outputted by the computer. The computer is for example operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The expression "acquiring data" for example encompasses (within the framework of a data processing method) the scenario in which the data are determined by the data processing method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the data processing method or program, for example from another program, a previous method step or a data storage medium, for example for further processing by the data processing method or program. The expression "acquiring data" can therefore also for example mean waiting to receive data and/or receiving the data. The received data can for example be inputted via an interface. The expression "acquiring data" can also mean that the data processing method or program performs steps in order to (actively) receive or retrieve the data from a data source, for instance a data storage medium (such as for example a ROM, RAM, database, hard drive, etc.), or via the interface (for instance, from another computer or a network). The data can be made "ready for use" by performing an additional step before the acquiring step.

In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. For example, the acquiring step does not involve an invasive step which would represent a substantial physical interference with the body, requiring professional medical expertise to be carried out and entailing a substantial health risk even when carried out with the required professional care and expertise. For example, the step of acquiring data, for example determining data, does not involve a surgical step and for example does not involve a step of treating a human or animal body using surgery or therapy. In order to distinguish the different data used by the present method, the data are denoted (i.e. referred to) as "XY data" and the like and are defined in terms of the information which they describe, which is then for example referred to as "XY information" and the like.

DESCRIPTION OF THE FIGURES

In the following, the invention is described with reference to the enclosed figure which represent preferred embodiments of the invention. The scope of the invention is not however limited to the specific features disclosed in the figures, wherein.

Figure 1:
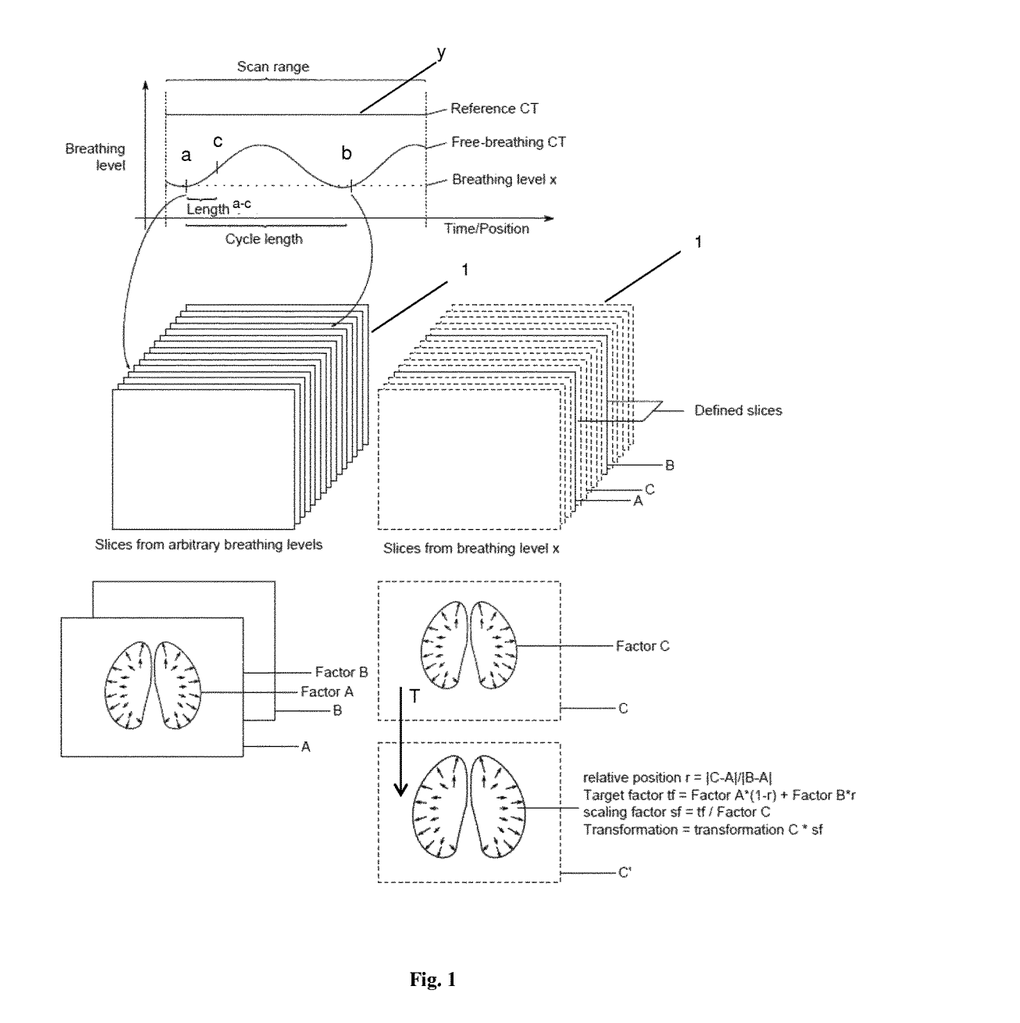
FIG. 1 illustrates the principles of the disclosed method.

FIG. 1 comprises a diagram showing the respiratory curve of a patient as the breathing level against time and/or position the imaging apparatus during acquisition of the reference CT (comprising the planning images) and the free-breathing CT (comprising the breathing images) and/or the time passed since initiation of the acquisition of the reference CT and the free-breathing CT, respectively. The planning images are included in a reference CT (comprising the planning images) which was taken at reference planning respiratory state y, which in the case shown by the diagram corresponds to a state of full inhalation. The term of breathing level corresponds to the amplitude of a respiratory state. A breathing level x is selected as the amplitude of the reference breathing respiratory state a associated with the reference breathing image A contained in the set 1 of breathing images which are included in the free-breathing CT. The comparative breathing image B is associated with a respiratory state b at breathing level x. For execution of the disclosed method, respiratory state b is equal to respiratory state a. Out of the set 1, two images, namely the reference breathing image A and the comparative breathing image B, are selected as images which are associated with the same respiratory state a. The geometry of the reference planning body part shown in the breathing reference image is denoted as Factor A, the geometry of the comparative breathing body part shown in the comparative breathing image B is denoted as Factor B. The positions along the rightward axis of the diagram at which the reference breathing image A and the comparative breathing image B and the target breathing image C associated with target respiratory state c were taken during acquisition of the free-breathing CT serve as a basis for calculating a relative position $r=|C-A|/|B-A|$, where A, B, and C denote the positions associated with the acquisition of the reference breathing image A, the comparative breathing image B and the target breathing image C, respectively. The target factor is calculated as $tf=Factor\ A*(1-r)+Factor\ B*r$ and serves as a basis for calculating the scaling factor sf as $sf=tf/Factor\ C$, where Factor*C denotes the geometry of the target body part shown in the target breathing image C. The derived transformation T between the geometry of the target body part Factor C shown in the target breathing image C and the geometry of the target body part C' as it is shown in the reference breathing respiratory state a (i.e. in the target planning image) is then calculated as $T=R*sf$, where R is the reference transformation between the reference planning image (which is associated with the reference planning respiratory state y) and the reference breathing image A.

Figure 2:
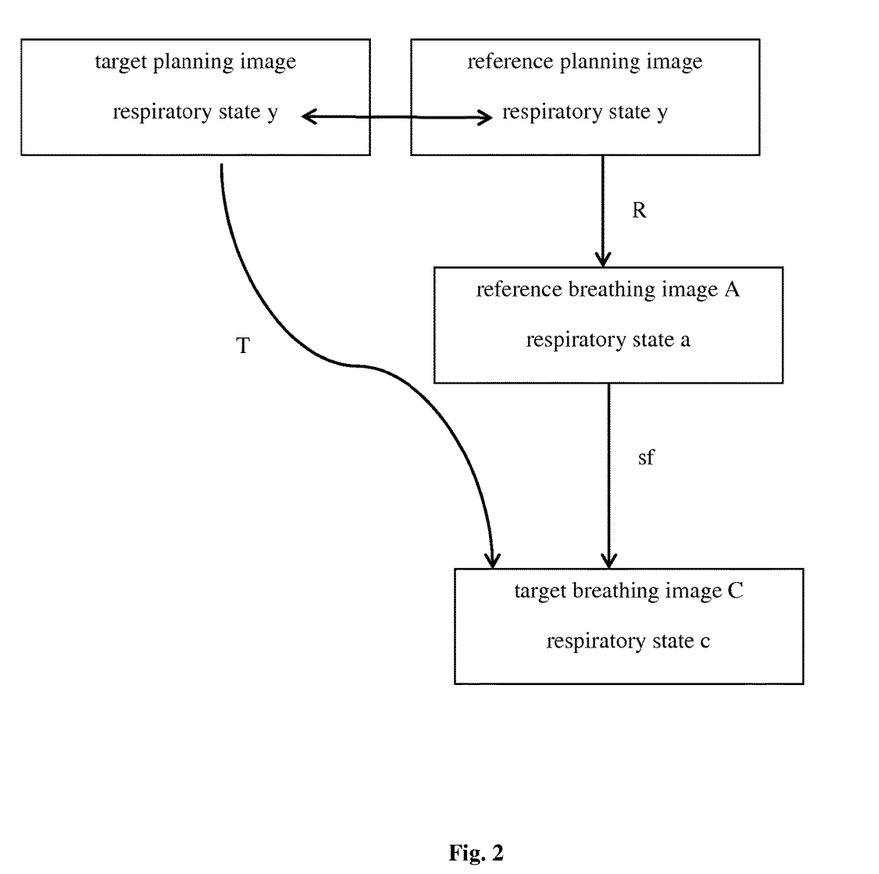
FIG. 2 illustrates the sequence of transformations determined by the disclosed method.

As illustrated by FIG. 2, the derived transformation T is a transformation for transforming the geometry of the target body part from the one shown in the target planning image (which is associated with the same reference planning respiratory state y as the reference planning image) into the geometry it would have in an image associated with the same respiratory state as the reference breathing image A (namely in the breathing reference respiratory state a) by application of the scaling factor sf to the reference transformation R, wherein the scaling factor sf defines a spatial relationship between the image features in the reference breathing image A and the image features in the target breathing image C.

The invention claimed is:

1. A radiotherapy system or radiosurgery system, comprising:
a treatment beam source; and
at least one computer having at least one processor that executes instructions stored on a computer readable storage medium to determine a transformation for determining a breathing state-dependent geometry of an anatomical body part of a patient's body, the instructions causing the at least one processor to:
acquire, by the at least one processor, planning image data describing a set of tomographic medical planning images describing each a different part of the anatomical body part in the same respiratory state called a reference planning respiratory state, wherein the anatomical body part is subject to respiratory movement and wherein the planning image data comprises a planning image called a reference planning image describing a part of the anatomical body part which is called a reference planning body part;
acquire, by the at least one processor, breathing image data describing a set of tomographic medical breathing images of the anatomical body part, wherein the breathing image data comprises a reference breathing image describing the reference planning body part in a respiratory state called a reference breathing respiratory state, which is different from the reference planning respiratory state, and a target breathing image describing at least another part of the anatomical body part, wherein the other part of the anatomical body part is called a target body part, in a respiratory state called a target respiratory state which is different from the reference planning respiratory state;

determine, by the at least one processor and based on the planning image data and the breathing image data, a reference transformation data called a reference transformation, between the geometry of the reference planning body part in the reference planning respiratory state and the geometry of the reference planning body part in the reference breathing respiratory state;

acquire, by the at least one processor, scaling factor data describing a scaling factor which describes a relationship between the geometry of the reference planning body part in the reference breathing respiratory state and the geometry of the target body part in the target respiratory state;

determine, by the at least one processor and based on the reference transformation and the scaling factor data, derived transformation data called a derived transformation between the geometry of the target body part in the reference planning respiratory state, and the geometry of the target body part in the reference breathing respiratory state wherein the at least one computer is operatively connected to the treatment beam source and controlling the treatment beam source to emit a treatment beam based on the derived transformation data.

2. A computer-implemented method for determining a transformation for determining a breathing state-dependent geometry of an anatomical body part of a patient's body, the method comprising executing, by at least one processor of at least one computer, steps of:

acquiring, by the at least one processor, planning image data describing a set of tomographic medical planning images describing each a different part of the anatomical body part in the same respiratory state called a reference planning respiratory state, wherein the anatomical body part is subject to respiratory movement and wherein the planning image data comprises a planning image called a reference planning image describing a part of the anatomical body part which is called a reference planning body part;

acquiring, by the at least one processor, breathing image data describing a set of tomographic medical breathing images of the anatomical body part, wherein the breathing image data comprises a reference breathing image describing the reference planning body part in a respiratory state called a reference breathing respiratory state, which is different from the reference planning respiratory state, and a target breathing image describing at least another part of the anatomical body part, wherein the other part of the anatomical body part is called a target body part, in a respiratory state called a target respiratory state which is different from the reference planning respiratory state;

determining, by the at least one processor and based on the planning image data and the breathing image data, a reference transformation data called a reference transformation, between the geometry of the reference planning body part in the reference planning respiratory state and the geometry of the reference planning body part in the reference breathing respiratory state;

acquiring, by the at least one processor, scaling factor data describing a scaling factor which describes a relationship between the geometry of the reference planning body part in the reference breathing respiratory state and the geometry of the target body part in the target respiratory state;

determining, by the at least one processor and based on the reference transformation and the scaling factor data, derived transformation data called a derived transformation between the geometry of the target body part in the reference planning respiratory state, and the geometry of the target body part in the reference breathing respiratory state;

controlling a treatment beam source based on the derived transformation data to activate the treatment beam source when the target body part is at a predetermined position.

3. The method according to claim 2, wherein the method is used for eliminating, by the at least one processor, an artefact contained in a slice image of a set of tomographic medical image data, wherein one of the tomographic medical breathing images including the artefact is selected, by the at least one processor, as the target breathing image in the target respiratory state, and another one of the tomographic medical breathing images not containing the artefact is selected, by the at least one processor, as the reference breathing image.

4. The method according to claim 2, wherein the breathing image data comprises a comparative breathing image describing a further part of the anatomical body part in the reference breathing respiratory state, which further part is called comparative breathing body part and is different from the reference body part and the target body part, wherein acquiring the scaling factor data comprises:

acquiring, by the at least one processor, image spacing data describing the spatial relationship between the positions at which the reference breathing image, the target breathing image and the comparative breathing image were generated; and determining, by the at least one processor, the scaling factor data based on the image spacing data and the reference breathing image data.

5. The method according to claim 4, wherein the spatial relationship is defined as the ratio r of the distance between the positions at which the reference breathing image and the target breathing image were generated, and the distance between the positions at which the reference breathing image and the comparative breathing image were generated.

6. The method according to claim 5, wherein a target factor is determined, by the at least one processor, by multiplying by the geometry of the reference planning body part in the reference breathing respiratory state and adding thereto the product of r and the geometry of the comparative breathing body part in the reference breathing respiratory state.

7. The method according to claim 2, wherein the target factor is determined, by the at least one processor, based on a function describing the expected geometries of different parts of the anatomical body part as a function of the position of the breathing image showing a part of the anatomical body part in the set of breathing images under the assumption that that part of the anatomical body part is in the reference planning respiratory state.

8. The method according to claim 6, wherein the scaling factor is determined, by the at least one processor, by dividing the target factor by the geometry of the target body part in the target respiratory state.

9. The method according to claim 5, comprising:
acquiring, by the at least one processor, imaging movement data describing the movement of a medical imaging apparatus relative to the anatomical body parts while it is being used for generating the breathing medical images;
acquiring, by the at least one processor, respiratory cycle data describing the time period required by the patient for a respiratory cycle;
determining, by the at least one processor, the comparative breathing image from the breathing images based on the imaging movement data and the respiratory cycle data.

10. The method according to claim 9, comprising:
acquiring, by the at least one processor, the comparative breathing image from the breathing image data based on the imaging movement data and a consistency optimization that uses metrics derived from reconstructed datasets.

11. The method according to claim 2, wherein the scaling factor is predetermined, by analysis of a plurality of tomographic image sets taken for a plurality of patients during respiratory movement.

12. The method according to claim 2, wherein the derived transformation is determined, by the at least one processor, by multiplying the reference transformation by the scaling factor.

13. The method according to claim 2, wherein the breathing image data was generated over the whole length of a breathing cycle of the patient and wherein the method is executed repeatedly until a breathing image has been used as a reference breathing image for each of the respiratory states described by the breathing image data.

14. The method according to claim 2, wherein the position of the reference body part in the target respiratory state is determined, by the at least one processor, by subjecting the reference planning image to the derived transformation.

15. A non-transitory computer-readable data storage medium storing a program having instructions which, when executed by at least one processor of at least one computer, causes the at least one computer to determine a transformation for determining a breathing state-dependent geometry of an anatomical body part of a patient's body, the instructions causing the at least one processor to perform the steps of:
acquiring, by the at least one processor, planning image data describing a set of tomographic medical planning images describing each a different part of the anatomical body part in the same respiratory state called a reference planning respiratory state, wherein the anatomical body part is subject to respiratory movement and wherein the planning image data comprise a planning image called a reference planning image describing a part of the anatomical body part which is called a reference planning body part;
acquiring, by the at least one processor, breathing image data describing a set of tomographic medical breathing images of the anatomical body part, wherein the breathing image data comprise a reference breathing image describing the reference planning body part in a respiratory state called a reference breathing respiratory state, which is different from the reference planning respiratory state, and a target breathing image describing at least another part of the anatomical body part, wherein the other part of the anatomical body part is called a target body part, in a respiratory state called a target respiratory state which is different from the reference planning respiratory state;
determining, by the at least one processor and based on the planning image data and the breathing image data, a reference transformation data called a reference transformation, between the geometry of the reference planning body part in the reference planning respiratory state and the geometry of the reference planning body part in the reference breathing respiratory state;
acquiring, by the at least one processor, scaling factor data describing a scaling factor which describes a relationship between the geometry of the reference planning body part in the reference breathing respiratory state and the geometry of the target body part in the target respiratory state;
determining, by the at least one processor and based on the reference transformation and the scaling factor data, derived transformation called a derived transformation between the geometry of the target body part in the reference planning respiratory state, and the geometry of the target body part in the reference breathing respiratory state;
controlling by the at least one processor, one of a treatment beam source or a patient support unit, based on the derived transformation data.

16. A radiotherapy system, comprising:
a treatment beam source;
a patient support unit;
at least one computer operably connected to the treatment beam source and the patient support unit, and having memory and instructions, the instructions executed by the at least one processor to:
acquire planning image data describing an anatomical body part in a reference planning respiratory state, wherein the anatomical body part is subject to respiratory movement and wherein the planning image data include a reference planning body part in a reference planning respiratory state;
acquire breathing image data describing a set of tomographic medical breathing images of the anatomical body part, the breathing image data including
a reference breathing image describing the reference planning body part in a reference breathing respiratory state; and
a target breathing image describing a target body part in a target respiratory state;
determine based on the planning image data and the breathing image data, a reference transformation, between the geometry of the reference planning body part in the reference planning respiratory state and the geometry of the reference planning body part in the reference breathing respiratory state;
acquire scaling factor data describing a scaling factor relating the geometry of the reference planning body part in the reference breathing respiratory state and the geometry of the target body part in the target respiratory state;
determine, based on the reference transformation and the scaling factor data, a derived transformation between the geometry of the target body part in the reference planning respiratory state, and the geometry of the target body part in the reference breathing respiratory state;
control at least one of the treatment beam source and patient support unit based on the derived transformation when treating the target body part.

* * * * *